United States Patent [19]

Nader

[11] Patent Number: 5,066,409
[45] Date of Patent: Nov. 19, 1991

[54] NOVEL ARYL ETHER SULFONES

[75] Inventor: Bassam S. Nader, Midland, Mich.

[73] Assignee: The Dow Chemical Company, Midland, Mich.

[21] Appl. No.: 581,616

[22] Filed: Sep. 12, 1990

[51] Int. Cl.$^5$ .................... C07C 147/10; C10M 1/42
[52] U.S. Cl. .................................. 252/48.2; 528/171; 528/173; 528/174; 528/175
[58] Field of Search ................ 252/48.2; 528/171, 173

[56] References Cited

U.S. PATENT DOCUMENTS

| | | |
|---|---|---|
| 2,998,453 | 8/1961 | Nichols . |
| 3,455,846 | 7/1969 | Bannister ........................ 252/48.2 |
| 3,455,866 | 7/1969 | D'Alessandro . |
| 3,455,868 | 7/1969 | D'Alessandro . |
| 3,634,354 | 1/1972 | Darsow et al. . |
| 3,719,714 | 3/1973 | Leslie et al. . |
| 3,759,956 | 9/1973 | Stapp ................................ 252/48.2 |
| 3,844,956 | 10/1974 | Nnandi ............................. 252/48.2 |
| 4,115,287 | 9/1978 | Colclough et al. ............... 252/48.2 |
| 4,303,776 | 12/1981 | Baron et al. . |
| 4,490,266 | 12/1984 | Hentschel et al. . |

FOREIGN PATENT DOCUMENTS

| | | |
|---|---|---|
| 0090870 | 10/1983 | European Pat. Off. . |
| 54-148835 | 11/1979 | Japan . |
| 1214700 | 12/1970 | United Kingdom . |

OTHER PUBLICATIONS

Fanta, "The Ullmann Synthesis of Biaryls", *Synthesis*, pp. 9-21 (1974).

Semmelhack et al., "Reaction of Aryl and Vinyl Halides with Zerovalent Nickel-Preparative Aspects and the Synthesis of Alnusone", J. Am. Chem. Soc. 1981, 103, 6460-6471.

*Primary Examiner*—Jacqueline V. Howard
*Assistant Examiner*—M. Nuzzolillo
*Attorney, Agent, or Firm*—Ann K. Galbraith

[57] ABSTRACT

Disclosed is an aryl ether sulfone of the following formula:

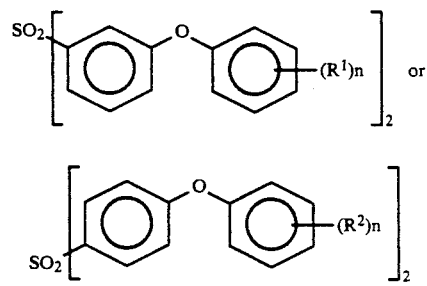

wherein $R^1$ is independently in each occurrence hydrogen, alkyl, alkoxy, aryl, aryloxy, polyhaloaryl, polyhaloaryloxy, polyhaloalkylaryl, or polyhaloalkylaryloxy, $R^2$ is independently in each occurrence hydrogen, alkyl, alkoxy, aryl, aryloxy, polyhaloaryl, polyhaloaryloxy, polyhaloalkylaryl, or polyhaloalkylaryloxy, and n is a whole number from 1 to 5. Also disclosed is a lubricant composition which comprises a lubricating fluid and an aryl ether sulfone as shown above, wherein the aryl ether sulfone is present in an amount sufficient to increase the lubricity of the lubricating fluid component.

21 Claims, No Drawings

NOVEL ARYL ETHER SULFONES

BACKGROUND OF THE INVENTION

This invention relates to aryl ether sulfones, and to their use as lubricating fluids and as lubricity-enhancing additives.

It is generally known that aryl ether sulfones are useful as lubricating fluids. For example, U.S. Pat. No. 2,998,453 discloses certain aryl ether sulfones which are taught to be useful as lubricants. However, such aryl ether sulfones may not be thermally stable at extremely high temperatures, such as temperatures above about 300° C., and may also have lubricating properties which are poorer than desired.

One type of lubricating fluids known to be useful for high temperature applications is the perfluoroalkyl ethers. However, such compounds are often insoluble or otherwise incompatible with most hydrocarbon, ester, and aromatic-based lubricating fluids, and have higher densities than are desired for such applications. In addition, such compounds give off hydrogen fluoride gas upon decomposition.

Another type of lubricating fluids known to be useful for high temperature applications are polyaryl ether fluids. However, such fluids have lubricating properties which are less than are desired for many applications.

SUMMARY OF THE INVENTION

In one aspect, this invention is an aryl ether sulfone of the following formula:

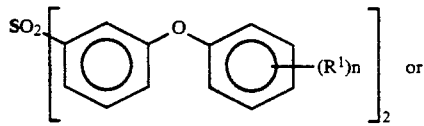

or

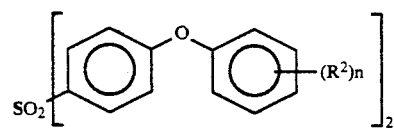

wherein $R^1$ is independently in each occurrence hydrogen, hydroxyl, alkyl, alkoxy, aryl, aryloxy, polyhaloaryl, polyhaloaryloxy, polyhaloalkylaryl, or polyhaloalkylaryloxy, $R^2$ is independently in each occurrence alkyl, alkoxy, aryl, aryloxy, polyhaloaryl, polyhaloaryloxy, polyhaloalkylaryl, or polyhaloalkylaryloxy, and n is a whole number from 1 to 5.

In a second aspect, this invention is a lubricant composition which comprises a lubricating fluid and the aforementioned aryl ether sulfone, wherein the aryl ether sulfone is present in an amount sufficient to increase the lubricity of the lubricating fluid.

The aryl ether sulfones of the invention are suitable lubricants and lubricity-enhancing additives for lubricating systems which use fluids stable under high temperatures as a base stock, and are advantageously soluble is such systems. The sulfones of the invention are useful in applications over a wide range of temperatures, such as −50° to 450° C. The sulfones of the invention have good lubricating properties and densities similar to hydrocarbon or polyaryl ether based fluids.

DETAILED DESCRIPTION OF THE INVENTION

The aryl ether sulfones of the first aspect of the invention are those of the formula:

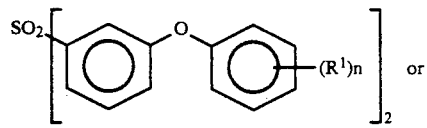

or

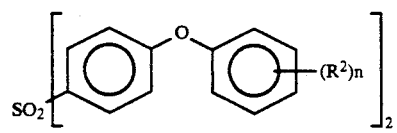

wherein $R_1$ and $R_2$ are as defined above.

The ring carbons of these compounds which do not have substituents as shown in the formula may optionally be substituted with other groups such as, for example, alkyl, alkoxy, aryloxy, polyhaloalkyl, polyhaloaryl, polyhaloalkoxy, polyhaloalkylaryl, or polyhaloalkylaryloxy having 1-20 carbon atoms: halogen: aryl: pyridinyl: benzimidazoyl: or benzothiazoyl. Preferably, $R^1$ is alkyl, alkoxy, aryl, aryloxy, polyhaloaryl, polyhaloaryloxy, polyhaloalkylaryl, or polyhaloalkylaryloxy. More preferably, $R^1$ or $R^2$ is polyhaloalkyl, and is most preferably perfluoroalkyl. Preferably, n is 1 or 2. If $R^1$ or $R^2$ is a polyhaloalkyl group, then the substituent is preferably in the meta position relative to the connecting ether group, since these compounds advantageously have lower pour points than the corresponding compounds with substituents in the para positions. However, it is generally preferable to use para-substituted compounds if suitable for the particular application due to their relative ease of manufacture, as will be discussed hereafter.

As used herein, the following terms refer respectively to the generic structures following the term:

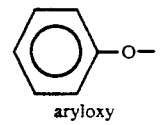

aryloxy

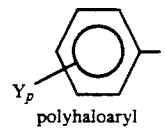

polyhaloaryl

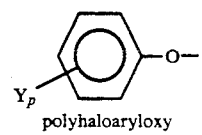

polyhaloaryloxy

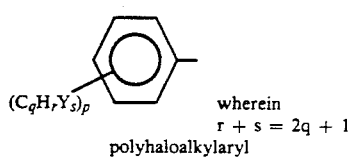

wherein
r + s = 2q + 1
polyhaloalkylaryl

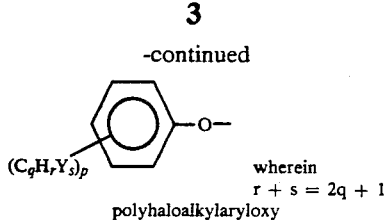

wherein
r + s = 2q + 1
polyhaloalkylaryloxy

pyridinyl

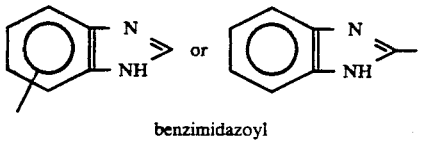

benzimidazoyl

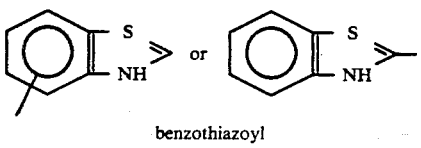

benzothiazoyl wherein Y is a halo moiety such as, fluoro, chloro, bromo, or iodo; p is a whole number from 1 to 5; and q is a whole number from 1 to 20.

Examples of the compounds of the invention include: bis[4-(3-trifluoromethylphenoxy)phenyl] sulfone, bis[3-(3-trifluoromethylphenoxy)phenyl] sulfone, bis[4-(4-trifluoromethoxyphenoxy)phenyl] sulfone, bis[4-(3-trifluoromethoxyphenoxy)phenyl] sulfone, bis[3-(4-trifluoromethoxyphenoxy)phenyl] sulfone, bis[3-(3-trifluoromethoxyphenoxy)phenyl] sulfone, bis[4-(3-pentafluoroethylphenoxy)phenyl] sulfone, bis[3-(3-pentafluoroethylphenoxy)phenyl] sulfone, bis[4-(4-pentafluoroethoxyphenoxy)phenyl] sulfone, bis[4-(3-pentafluoroethoxyphenoxy)phenyl] sulfone, bis[3-(4-pentafluoroethoxyphenoxy)phenyl] sulfone, bis[3-(3-pentafluoroethoxyphenoxy)phenyl] sulfone, bis[4-(4-fluorophenoxy)phenyl] sulfone, bis[4-(3-fluorophenoxy)phenyl] sulfone, bis[3-(4-fluorophenoxy)phenyl] sulfone, bis[3-(3-fluorophenoxy)phenyl] sulfone, bis[4-(4-(3-trifluoromethyl)phenoxy)phenoxyphenyl] sulfone, bis[4-(3-(3-trifluoromethyl)phenoxy)phenoxyphenyl] sulfone, bis[3-(3-(3-trifluoromethyl)phenoxy)phenoxyphenyl] sulfone, bis[3-(4-(3-trifluoromethyl)phenoxy)phenoxyphenyl] sulfone.

The aryl ether sulfones of the invention may be prepared, for example, by reacting a sulfonyldiphenol with an aryl halide in the presence of an aqueous or nonaqueous base under reaction conditions sufficient to form the corresponding aryl ether sulfone. The sulfones may also be prepared by reacting a dihaloaryl sulfone with a phenoxide under reaction conditions sufficient to form the corresponding aryl ether sulfone. These two methods are illustrated below:

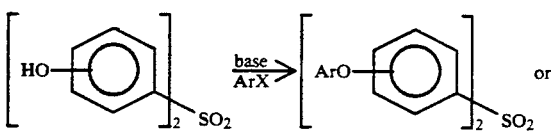

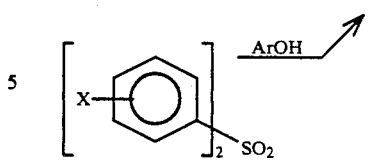

For example, 4,4'-dihydroxydiphenyl sulfone may be reacted with an aryl bromide to yield the corresponding aryl ether sulfone.

The reaction to form the aryl ether sulfones of the invention is preferably carried out in the presence of a solvent. Suitable solvents include, for example, polar aprotic solvents such as pyridine, benzene, quinoline, diglyme, dimethyl sulfoxide (DMSO), dimethyl formamide (DMF), n-methyl pyrrolidinone (NMP), N,N'-dimethylacetamide, hexamethylphosphoramide (HMPA), sulfolane, or toluene, but is preferably a water-soluble solvent such as pyridine, since such a solvent may be easily removed from the reaction mixture. In addition, this reaction is preferably carried out in the presence of a catalyst such as, for example, a copper salt such as cuprous chloride, or a copper compound as described, for example, in Jukes, A. E. "The Organic Chemistry of Copper" in *Advanced Organometallic Chemistry*, No. 12, pp. 215-321 (1974).

The aryl ether sulfones of the invention may be used as lubricating fluids, and may also be used as lubricity-enhancing additives for other lubricating fluids as a lubricant composition. Suitable lubricating fluids which may be used with the aryl ether sulfones of the invention include, for example, hydrocarbon lubricants such as mineral oil; alpha-olefin fluids; silicone fluids and greases; polyalkyl ether fluids; perfluoroalkylpolyether fluids and greases; ester lubricants such as pentaerythritol esters and trimethylol alkane esters; polyaryl ether fluids; and phosphazene fluids. Preferably, the lubricating fluid is a phosphazene fluid or polyaryl ether fluid, for their thermal stability. When a phosphazene is used as a lubricating fluid, it is preferably a phosphazene with fluorinated phenoxy and trifluoroalkyl phenoxy groups as described, for example in copending applications Ser. No. 417,363, filed Oct. 5, 1989, which is hereby incorporated by reference in its entirety. Of these phosphazenes, particularly preferred are those wherein the ratio of fluorinated phenoxy groups:trifluoroalkyl phenoxy groups is about 1:2, since such lubricants are useful over extended temperature ranges. Most preferably, the lubricating fluid is a polyaryl ether fluid, since such fluids have high thermal stability.

The aryl ether sulfones are employed in the lubricant composition in an amount sufficient to increase the lubricity of the lubricating fluid. Preferably, the aryl ether sulfones are employed in a concentration, based on the weight of the lubricating fluid component, of at least about 0.1 percent, more preferably at least about 0.5 percent, and most preferably at least about 1 percent; and preferably no greater than about 20 percent, more preferably no greater than about 10 percent, and most preferably no greater than about 5 percent. To prepare a solution of the aryl ether sulfone in the lubricant composition, it is preferable to first dissolve the compound in an organic solvent such as, for example, methylene chloride, and to mix this solution with a solution of the lubricant composition in an organic solvent. The mixture is then preferably filtered to remove solid impurities and any solvents are evaporated from the mixture.

The aryl ether sulfones of the invention provide a lubricant composition with enhanced lubricity, relative to lubricant or heat-transfer systems which do not contain such compounds. Such compounds are especially useful as additives in high temperature lubricant basestocks which may have the thermal and oxidative stability to withstand high temperature applications, such as in jet aircraft engines, but which have lubricating properties which are less than desired. An example of such a lubricant basestock is a polyarylether fluid. The lubricity of lubricant compositions may be measured by applying a standard test method as described in ASTM D-2783, "Standard Method for Measurement of Extreme Pressure Properties of Lubricating Fluids (Fourball Method)." In addition, the aryl ether sulfones of the invention are advantageously thermally and oxidatively stable when used in high temperature applications, and are advantageously soluble when used in such systems.

ILLUSTRATIVE EMBODIMENTS

The following examples are given to illustrate the invention and should not be interpreted as limiting it in any way. Unless stated otherwise, all parts and percentages are given by weight. All reactions requiring anhydrous conditions are performed in oven-dried glassware which was cooled under nitrogen. Thin layer chromatography (TLC) is performed on glass plates precoated with 0.25 mm of silica gel (Analtech, Inc., silica gel GHLF). Flash chromatography is performed on 230-400 mesh silica gel 60. Melting points are determined in open capillary tubes, and are uncorrected.

EXAMPLE 1

Preparation of 3,3'-diiododiphenyl sulfone

The reaction is performed in a 1 L beaker equipped with a magnetic stirring bar and cooled to 0° C. in an ice bath. The beaker is charged with sulfuric acid (12 mL. 95% w/w), water (55 mL), and 3,3'-diaminodiphenyl sulfone (15.0 g, 60.4 mmol). The mixture is stirred until the sulfone is completely dissolved (approximately 20 minutes), and the temperature is kept at 0° C. with the addition of 20 g of ice. Sodium nitrite (8.34 g, 121 mmol) in water (40 mL) is added dropwise below the surface of the reaction mixture, keeping the temperature below 5° C. The color darkens somewhat after the addition is complete, and it is left to stir for 10 minutes. Urea (0.25 g) is added to remove any of the excess sodium nitrite from solution. Potassium iodide (20.06 g, 121 mmol) in water (40 mL) is added slowly to the reaction mixture. Immediately gas evolution is evident, and the mixture turned dark brown. The mixture is left to stir for 3 hours until gas evolution subsided. The aqueous layer is removed, and the organic layer is washed with 10% NaOH (500 mL). Then it is diluted with CH₂Cl₂ and washed with water (2 L) and saturated NaHCO₃ (500 mL). Drying (MgSO₄), filtration and solvent removal on the rotary evaporator afforded 21.2 g of a dark solid. This solid is dissolved in CH₂Cl₂ and 10.0 g of decolorizing carbon is added. The carbon is filtered off, and the solvent is removed to leave 16.4 g of a yellow solid. It is recrystallized from methanol, and then passed through a short silica gel column with CH₂Cl₂ as the eluent to leave 12.2 g (43% yield) of a white crystalline solid, m.p. 110-114° C.

IR, $^1$H-NMR, and $^{13}$C-NMR data are consistent with the structure of

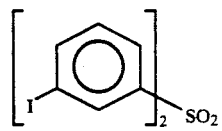

Preparation of bis[3-phenoxyphenyl] sulfone

All apparatus is rigorously dried and flushed with nitrogen before use. The reaction is performed in a 250 mL 3-necked flask equipped with a mechanical stirrer, a reflux condenser topped with a nitrogen inlet tube, and a stopper. The flask is charged with methanol (20 mL) and sodium (1.00 g, 4.35 mmol). After all of the sodium has been consumed the methanol is distilled from the flask, and the last traces are removed by azeotropic distillation with benzene. Pyridine (125 mL) and 3,3'-diiododiphenyl sulfone (10.0 g, 21.3 mmol) are added to the reaction mixture, followed with phenol (4.50 g, 47.8 mmol) and cuprous chloride (4.21 g, 42.6 mmol), and the mixture is left to stir at reflux for 24 hours. Then it is analyzed by TLC, which shows three spots ($R_f$=0.00, 0.50, 0.64; CH₂Cl₂). The reaction mixture is cooled, and filtered with the aid of ether (200 mL). The ethereal phase is washed successively with water (250 mL), 5% HCl (2×250 mL), saturated NaHCO₃ (200 mL), and brine (200 mL). Then it is dried with MgSO₄, and the solvents are removed on the rotary evaporator to leave a dark yellow oil. Purification is accomplished by column chromatography on flash grade silica gel using a 1:1 mixture of hexane/CH₂Cl₂ as eluent. It is determined that the top spot by TLC is the desired product. This afforded 2.43 g (28.4%) of the desired product as a colorless oil.

IR, $^1$H-NMR, and $^{13}$C-NMR data are consistent with the structure of:

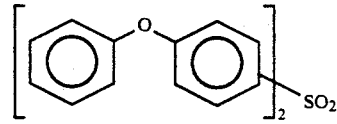

EXAMPLE 2

Preparation of bis[4-(3-trifluoromethylphenoxy)phenyl] sulfone

All apparatus is rigorously dried and flushed with nitrogen before use. The reaction is performed in a 250 mL 3-necked flask equipped with a mechanical stirrer, a reflux condenser topped with a nitrogen inlet tube, and a stopper. The flask is charged with 3-trifluoromethylphenol (11.29 g, 69.7 mmol), 4,4'-dichlorodiphenyl sulfone (10.00 g, 34.8 mmol), K₂CO₃ (15.00 g, 109 mmol) and DMF (125 mL). The reacting mixture is stirred and heated at reflux for 12 hours. The mixture is analyzed by gas chromatography, which showed that almost no starting materials remained. The reaction mixture is diluted with water, and the aqueous layer is removed to leave an oil. This oil is diluted with ether and washed with 5% NaOH to remove any acidic species. It is then washed with brine, dried with MgSO₄, and the solvent removed on the rotary evaporator to leave a white crystalline solid. This solid is purified by column chromatography on flash grade silica gel using a 1:1 mixture of CH₂Cl₂/Hexane as eluent. Further purification is accomplished by recrystallization of the white solid from ethanol to give white, diamond-shaped crystals (11.08 g, 59%), m.p. 96.5–97.5° C.

IR, $^1$H-NMR, and $^{13}$C-NMR data are consistent with the structure of:

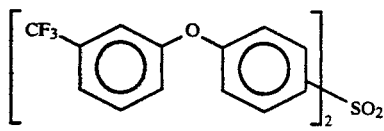

EXAMPLE 3

Preparation of bis3-(3-trifluoromethylphenoxy)phenyl] sulfone

All apparatus is rigorously dried and flushed with nitrogen before use. The reaction is performed in a 250 mL 3-necked flask equipped with a mechanical stirrer, a reflux condenser topped with a nitrogen inlet tube, and a stopper. The flask is charged with methanol (20 mL) and sodium (0.98 g, 42.5 mmol). After all of the sodium has been consumed the methanol is distilled from the flask. The last traces of methanol are removed by azeotropic distillation with benzene. Pyridine (125 mL) and 3-iodophenylsulfone (10.0 g, 21.3 mmol) are added, followed by 3-trifluoromethylphenol (6.90 g, 42.5 mmol) and cuprous chloride (4.21 g, 42.5 mmol), and the mixture is left to stir at reflux for 24 hours. Then it is analyzed by TLC, which shows four spots ($R_f$=0.00, 0.53, 0 65, 0.75; CH₂Cl₂). The reaction mixture is cooled, and filtered with the aid of ether (200 mL). The ethereal phase is washed successively with water (250 mL), 5% HCl (2×250 mL), saturated NaHCO₃ (200 mL) and brine (200 mL). Then it is dried (MgSO₄) and the solvents are removed on the rotary evaporator to leave 8.95 g of a dark yellow oil. Purification is accomplished by column chromatography on flash grade silica gel using a 1:1 mixture of hexane/CH₂Cl₂ as eluent. It is determined that the top spot by TLC is the desired product. This afforded 1.15 g (10%) of the desired product as a colorless oil.

IR, $^1$H-NMR, and $^{13}$C-NMR data are consistent with the structure of:

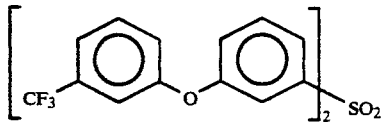

EXAMPLE 4

Preparation of 4-(3-trifluoromethylphenoxy) bromobenzene

The reaction is performed in a 1 L 3-necked flask equipped with a mechanical stirrer, a Dean-Stark trap topped with a condenser and a nitrogen bubbler, and a stopper. The flask is flushed with nitrogen and charged firstly with potassium hydroxide (22.4 g, 0.4 mol), α,α,α-trifluoro-m-cresol (64.8 g, 0.4 mol), and toluene (500 mL). The mixture is stirred and heated at reflux for 2 h, during which water collected in the trap (ca. 6 mL). 1,4-Dibromobenzene (94.4 g, 0.42 mol) and cuprous chloride (39.6 g, 0.4 mol) are added, and heating a reflux is continued for another 18 h. The reaction mixture is analyzed by capillary GC which shows ca.45% of the title product along with ca.10% of the dialkylation product, with the rest being starting materials. The mixture is filtered with the aid of ether (200 mL), and washed successively with 2×100 mL portions of 5% HCl (to remove any residual copper impurities), water, and brine. It is then dried (MgSO₄) and concentrated on the rotary evaporator to a red oily residue. TLC (silica gel) shows four components ($R_f$=0.00, 0.15, 0.35, 0.70, CH₂Cl₂). Fractional distillation afforded 42.9 g (34%) of the title compound, distilling at 112–116° C. @ 1 mm. Also obtained was 12.1 g (10.5%) of the dialkylation product, distilling at 160–165° C. @ 1 mm.

IR, $^1$H-NMR, and $^{13}$C-NMR data are consistent with the structure of:

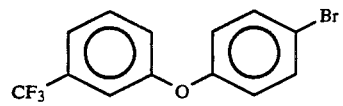

Preparation of bis[4-(4-(3-trifluoromethylphenoxy) phenoxy)phenyl] sulfone

All apparatus is rigorously dried and flushed with nitrogen before use. The reaction is performed in a 100 mL 3-necked flask equipped with a mechanical stirrer, a reflux condenser topped with a nitrogen inlet tube, and a stopper. The flask is charged with methanol (20 mL) and sodium (0.735 g, 31.8 mmol). After all of the sodium has been consumed the methanol is distilled from the flask. The last traces of methanol are removed by azeotropic distillation with benzene. Pyridine (40 mL) and 4,4'-dihydroxydiphenyl sulfone (4 g, 15.9 mmol) are added, followed by 4-(3-trifluoromethylphenoxy)-bromo-benzene (10.08 g, 31.8 mmol) and cuprous chloride (3.15 g, 31.8 mol), and the mixture is left to stir at reflux for 48 hours. The reaction mixture is analyzed by TLC, which shows three spots ($R_f$=0.00, 0.38, 0.95; CH₂Cl₂), with the upper spot being starting material and the middle spot being product. The mixture is cooled and filtered with the aid of ether (200 mL). The ethereal phase is washed successively with water (250 mL), 5% HCl (2×250 mL), saturated NaHCO₃ (200 mL) and brine (200 mL), then is dried with MgSO₄, and the solvents are removed on the rotary evaporator to leave 10.98 g of a yellow oil. Purification is accomplished by column chromatography on flash grade silica gel using a 1:1 mixture of hexane/CH₂Cl₂ as eluent. The product is obtained as a thick viscous oil (2.15 g, 18.7%).

IR, $^1$H-NMR, and $^{13}$C-NMR data are consistent with the structure of:

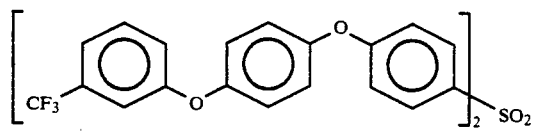

EXAMPLE 5

Preparation of 3-(3-trifluoromethylphenoxy) bromobenzene

The reaction is performed in a 1 L 3-necked flask equipped with a mechanical stirrer, a Dean-Stark trap topped with a condenser and a nitrogen bubbler, and a stopper. The flask is flushed with nitrogen and charged firstly with potassium hydroxide (22.4 g, 0.4 mol), α,α,α-trifluoro-m-cresol (64.8 g, 0.4 mol), and toluene (500 mL). The mixture is stirred and heated at reflux for 2 h, during which time water collected in the trap (ca. 6mL). 1,3-Dibromobenzene (50 mL, 0.42 mol) and cuprous chloride (39.6 g, 0.4 mol) are added to the reaction mixture, and heating at reflux is continued for another 18 h. Then it is analyzed by capillary GC, which shows ca.45% of the title product along with ca.12.5% of the product resulting from dialkylation, with the rest being starting materials. The reaction mixture is filtered with the aid of ether (200 mL), and washed successively with 2×100 mL portions of 5% HCl (to remove any residual copper impurities), water, and brine. It is dried with (MgSO4) and concentrated on the rotary evaporator to a red oily residue. Fractional distillation afforded 47 g (38%) of the title compound, distilling at 113–117° C. @ 1 mm. Also, 112 g (10.5%) of the dialkylation product is obtained, distilling at 160–165° C. @ 1 mm. Other fractions from the distillation show mixtures containing the desired product, but no further effort is made to obtain the rest of it.

IR, $^1$H-NMR, and $^{13}$C-NMR data are consistent with the structure of:

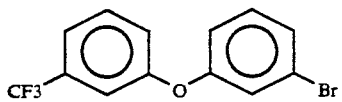

Preparation of bis[4-(3-trifluoromethylphenoxy) phenoxy)phenyl] sulfone

All apparatus is rigorously dried and flushed with nitrogen before use. The reaction is performed in a 100 mL 3-necked flask equipped with a mechanical stirrer, a reflux condenser topped with a nitrogen inlet tube, and a stopper. The flask is charged with methanol (20 mL) and sodium (0.735 g, 31.8 mmol). After all of the sodium has been consumed the methanol is distilled from the flask. The last traces of methanol are removed by azeotropic distillation with benzene. Pyridine (40 mL) and 4,4'-dihydroxydiphenyl sulfone (4 g, 15.9 mmol) are added to the reaction mixture. The remaining benzene is distilled from the flask. This is followed by addition of 3-(3-trifluoromethylphenoxy)bromobenzene (10.08 g, 31.8 mmol) and cuprous chloride (3.15 g, 31.8 mol), and the mixture is stirred and heated at reflux for 48 hours. The reaction mixture is analyzed by TLC to determine the extent of conversion to desired products. Three spots are found (R$_f$=0.00, 0.39, 0.95; CH$_2$Cl$_2$) with the upper spot being starting material and the middle spot being product. The mixture is cooled and filtered with the aid of ether (200 mL), and the ethereal phase was washed successively with water (250 mL), 5% HCl (2×250 mL), saturated NaHCO$_3$ (200 mL) and brine (200 mL). The ether layer is dried with MgSO$_4$, and the solvents are removed on the rotary evaporator to leave 10.8 g of a yellow oil. Purification is accomplished by column chromatography on flash grade silica gel using successive mixtures of hexane/CH$_2$Cl$_2$ (3:1, 2:1 and 1:1 (v/v)) for elution. This afforded 1.54 g (13.4% yield) of the desired product.

IR, $^1$H-NMR, and $^{13}$C-NMR data are consistent with the structure of:

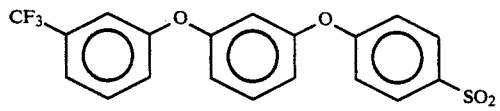

EXAMPLE 6

Preparation of 3-(3-trifluoromethylphenoxy)phenol

All apparatus is rigorously dried and flushed with nitrogen before use. The reaction is performed in a 500 mL 3-necked flask equipped with a mechanical stirrer, a reflux condenser topped with a nitrogen inlet tube and a stopper. The flask is charged with methanol (100 mL) and sodium (10.0 g, 0.43 mol). After all of the sodium has been consumed the methanol is distilled from the flask, and the last traces are removed by azeotropic distillation with benzene. Pyridine (250 mL) and resorcinol (35.0 g, 0.32 mol) are added to the reaction mixture, followed by 3-(3-trifluoromethyl phenoxy)bromobenzene (50.0 g, 0.22 mol) and cuprous chloride (20.0 g, 0.20 mol), and the mixture is left to stir at reflux for 24 hours. Capillary GC analysis shows that ca. 87% of the mixture is the desired monoalkylation product, the rest being dialkylation product. The mixture is cooled and filtered with the aid of ether (200 mL). The ethereal phase is washed successively with water (250 mL), 5% HCl (2×250 mL), saturated NaHCO$_3$ (200 mL) and brine (200 mL). Then it is dried with MgSO$_4$, and the solvents are removed on the rotary evaporator to leave 38 g of a dark oily residue. Purification is accomplished by fractional distillation in vacuo. The second fraction (distilling at 132° C. @ 1.5 mm) consisted of pure monoalkylation product (colorless oil, 25.20 g, 44.6% yield). The dialkylation product is not isolated.

IR, $^1$H-NMR, and $^{13}$C-NMR data are consistent with the structure of:

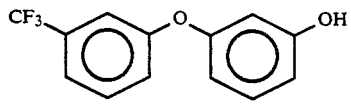

Preparation of bis[3-(3-(3-trifluoromethylphenoxy) phenoxy)phenyl] sulfone

All apparatus is rigorously dried and flushed with nitrogen before use. The reaction is performed in a 100 mL 3-necked flask equipped with a mechanical stirrer, a reflux condenser topped with a nitrogen inlet tube and a stopper. The flask is charged with methanol (20 mL) and sodium (0.196 g, 8.5 mmol). After all of the sodium has been consumed, the methanol is distilled off, removing the last traces by azeotropic distillation with benzene. Pyridine (50 mL) and 3,3'-diiododiphenyl sulfone (2 g, 4.3 mmol) are added to the reaction mixture. The remaining benzene is distilled off, and 3-(3-trifluoromethylphenoxy)bromobenzene (2.16 g, 8.5 mmol) and cuprous chloride (0.84 g, 8.5 mmol) are added. The mixture is left to stir at reflux for 48 hours, then it is analyzed by TLC. Four spots are observed (R$_f$=0.00, 0.65, 0.73 and 0.82; CH$_2$Cl$_2$). The mixture is cooled and filtered with the aid of ether (200 mL). The ethereal solution is washed successively with water (250 mL), 5% HCl (2×250 mL), saturated NaHCO$_3$ (200 mL) and brine (200 mL), then is dried (MgSO$_4$) and the solvents are removed on the rotary evaporator to leave 2.10 g of a dark yellow oil. Purification is accomplished by column chromatography on flash grade silica gel, using a 1:1 mixture of hexane-CH$_2$Cl$_2$ as eluent. It is determined that the top spot by TLC is the desired product. This afforded 0.58 g (18.9% yield) of the product.

IR, $^1$H-NMR, and $^{13}$C-NMR data are consistent with the structure of:

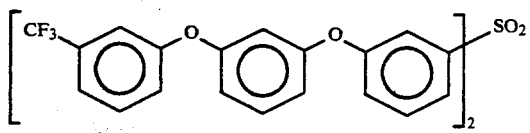

What is claimed is:

1. A compound of the following formula:

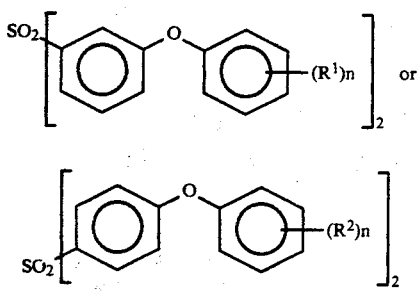

wherein R$^1$ is independently in each occurrence hydrogen, hydroxyl, alkyl, alkoxy, aryl, aryloxy, polyhaloaryl, polyhaloaryloxy, polyhaloalkylaryl, or polyhaloalkylaryloxy, R$^2$ is independently in each occurrence alkyl, alkoxy, aryl, aryloxy, polyhaloaryl, polyhaloaryloxy, polyhaloalkylaryl, or polyhaloalkylaryloxy, and n is a whole number from 1 to 5.

2. The compound of claim 1 represented by the formula:

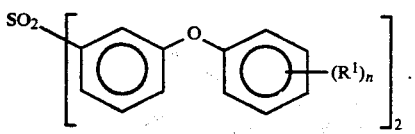

3. The compound of claim 2 wherein R$^1$ is polyhaloalkyl.

4. The compound of claim 3 wherein R$^1$ is perfluoroalkyl.

5. The compound of claim 1 wherein n is 1 or 2.

6. The compound of claim 1 represented by the formula:

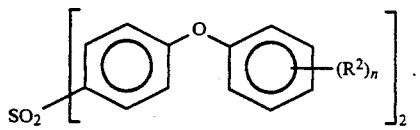

7. The compound of claim 2 wherein R$^1$ is polyhaloalkyl.

8. The compound of claim 3 wherein R$^1$ is perfluoroalkyl.

9. The compound of claim 1 wherein n is 1 or 2.

10. A lubricant composition which comprises a lubricating fluid and the compound of claim 1, wherein the compound is present in an amount, based on the weight of the lubricating fluid component, of at least about 0.1 percent.

11. The lubricant composition of claim 10 wherein the compound is present in an amount, based on the weight of the lubricating fluid component, of at least about 1 percent.

12. The lubricant composition of claim 10 wherein the lubricating fluid comprises a phosphazene compound.

13. The lubricant composition of claim 10 wherein the lubricating fluid comprises a polyaryl ether compound.

14. A lubricant composition which comprises a lubricating fluid and the compound of claim 2, wherein the compound is present in an amount, based on the weight of the lubricating fluid component, of at least about 0.1 percent.

15. The lubricant composition of claim 14 wherein the lubricating fluid comprises a phosphazene compound.

16. The lubricant composition of claim 14 wherein the lubricating fluid comprises a polyaryl ether compound.

17. The lubricant composition of claim 14 wherein the compound is present in an amount, based on the weight of the lubricating fluid component, of at least about 1 percent.

18. A lubricant composition which comprises a lubricating fluid and the compound of claim 5, wherein the compound is present in an amount, based on the weight of the lubricating fluid component, of at least about 0.1 percent.

19. The lubricant composition of claim 18 wherein the lubricating fluid comprises a phosphazene compound.

20. The lubricant composition of claim 18 wherein the lubricating fluid comprises a polyaryl ether compound.

21. The lubricant composition of claim 18 wherein the compound is present in an amount, based on the weight of the lubricating fluid component, of at least about 1 percent.

* * * * *